United States Patent

Konya et al.

(10) Patent No.: US 8,333,713 B2
(45) Date of Patent: Dec. 18, 2012

(54) LANCET COMPRISING A TEST REGION

(75) Inventors: Ahmet Konya, Ludwigshafen (DE); Christian Hoerauf, Oftersheim (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/195,536

(22) Filed: Aug. 1, 2011

(65) Prior Publication Data

US 2011/0295154 A1 Dec. 1, 2011

Related U.S. Application Data

(63) Continuation of application No. PCT/EP2010/000460, filed on Jan. 27, 2010.

(30) Foreign Application Priority Data

Feb. 12, 2009 (EP) .................................. 09001937

(51) Int. Cl.
*A61B 5/00* (2006.01)
(52) U.S. Cl. ....................................................... 600/583
(58) Field of Classification Search .................. 600/583, 600/584; 435/4; 606/181–183
See application file for complete search history.

(56) References Cited

U.S. PATENT DOCUMENTS

| 2006/0293611 A1 | 12/2006 | Calasso et al. |
| 2007/0173740 A1* | 7/2007 | Chan et al. ..................... 600/583 |
| 2008/0082023 A1 | 4/2008 | Deck et al. |

FOREIGN PATENT DOCUMENTS

| EP | 1 360 933 A1 | 11/2003 |
| EP | 1 961 381 A1 | 8/2008 |
| WO | WO 2005/084530 A2 | 9/2005 |

OTHER PUBLICATIONS

International Patent Application No. PCT/EP2010/00460 International Preliminary Examination Report mailed May 16, 2011.
International Patent Application No. PCT/EP2010/00460 International Search Report mailed Apr. 26, 2010.

* cited by examiner

*Primary Examiner* — Brian Szmal
(74) *Attorney, Agent, or Firm* — Woodard, Emhardt, Moriarty, McNett & Henry LLP

(57) ABSTRACT

The invention relates to a lancet, comprising a base body (2), which has a test region (3) on an upper face for analyzing a body fluid sample, a lancing element (4) extending from the base body (2) for puncturing the skin of a patient, and a capillary structure (5) for transporting a body fluid sample from the lancing element (4) to the test region (3). According to the invention, the capillary structure (5) comprises a section that causes fluid to be transported in a direction that, in a top view of the upper face of the base body (2), has a component perpendicular to the longitudinal direction of the lancing element (4).

10 Claims, 2 Drawing Sheets

LANCET COMPRISING A TEST REGION

CROSS-REFERENCE TO RELATED APPLICATION

This application is a continuation of International Patent Application No. PCT/EP2010/000460 filed Jan. 27, 2010, which claims the benefit of European Patent Application No. 09001937.3 filed Feb. 12, 2009, the entire disclosures of which are hereby incorporated by reference.

FIELD OF THE INVENTION

The invention relates to a lancet having the features listed in the preamble of claim 1, as that which is known from EP 1 360 933 A1 or WO 2005/084530 A2. Such a lancet comprises a base body having a test region for analyzing a body fluid sample, a lancing element originating from the base body for puncturing the skin of a patient and extending in a piercing direction, and a capillary structure for transporting a body fluid sample from the lancing element to the test region. The invention further relates to a lancing system comprising a lancing device and such lancets.

BACKGROUND

Lancets, which together with matching hand-held devices form a lancing system, are used by diabetics, for example, who must check their blood sugar level several times a day and for this purpose require a body fluid sample obtained by a puncture wound. The constant goal in developing such lancing systems is to design them as small and compact as possible. This applies not only to hand-held devices for measuring an analyte concentration, for example the glucose concentration or the lactate concentration, but in particular to the lancets required by hand-held devices. The smaller the lancets are, the larger is the supply of lancets that can be carried in a hand device.

SUMMARY

It is therefore an object of the invention to show a way of how a compact lancing system for analyzing a body fluid sample can be implemented.

This object is achieved by a lancet having the characteristics of claim 1. Advantageous refinements of the invention are the subject matter of the dependent claims. The invention further achieves this object by a lancing system comprising lancets according to the invention and by a lancing device according to claim 15.

In a top view of the upper face, the lancing element and the test region are disposed laterally offset in relation to one another on a lancet according to the invention, and the capillary structure has a section that transports fluid sideways.

In order to transport fluid sideways, the capillary structure can comprise, for example, a section that runs transversely to the longitudinal direction of the lancing element, e. g. perpendicularly or obliquely to the longitudinal direction of the lancing element, when seen in the top view. The section in question may be rectilinear, but does not have to be. It is therefore also possible for this section of the capillary structure to run in a curve as viewed from above.

Generally speaking, the capillary structure can comprise a section that causes fluid to be transported in a direction that, in a top view of the upper face of the base body, has a component perpendicular to the longitudinal direction of the lancing element. The direction can optionally have further components, which run in the longitudinal direction of the lancing element or perpendicular to the upper face.

The arrangement of the capillary structure according to the invention makes it possible to place the test region laterally offset from the lancing element with respect to the longitudinal direction of the lancing element, so that the test region is not located in a direct line behind the lancing element. It is therefore possible with a lancet according to the invention to enable coupling to a lancing drive of a lancing device without impairing the analysis of a body fluid sample in the test region, even if the lancet is very small.

In a lancet according to the invention, the coupling region to which the lancing drive of a lancing device is coupled can be disposed in a straight line behind the lancing element and alongside to the test region. In this way, the length of the lancet can be considerably shortened, without limiting the function thereof.

In a lancing system according to the invention, the lancing drive of a lancing device can notably be coupled to the lancet behind the lancing element—minimizing moments of tilt and therefore painful vibrations—and cause a rectilinear piercing movement. By placing the test region laterally beside to the coupling region, the test region remains accessible for a measuring unit. Advantageously, a measurement can be conducted at the test region of a lancet according to the invention while the lancet is coupled to the lancing drive. Following a puncture, no complex repositioning with respect to a measuring unit is therefore required with a lancet according to the invention. The hand device of a lancing system according to the invention can thus make do with a relative simple and cost-effective mechanism, despite small lancets and small sample quantities.

According to an advantageous refinement of the invention, the capillary structure is designed as a capillary channel, for example as a groove or a slot. Such a groove or slot can be open or it can be covered by a cover, for example film or foil. The capillary structure preferably has a hydrophilic surface, which can be achieved in particular by way of a hydrophilic coating, for example using heparin. A capillary structure shall be understood to mean a structure that causes fluid transport by capillary forces.

The capillary channel preferably has a bend or a curve. It is particularly preferred for the capillary channel to have a cross-sectional surface, in the region of the bend or curve, that is no larger than in an adjoining section. By rounding the corners of a bend, an increase in the distance between opposing edges of the channel in the region of the bend can be prevented, whereby a consistent cross-sectional surface is ensured. The cross-sectional surface should be oriented in each case perpendicular to the local flow direction.

According to a further advantageous refinement of the invention, the capillary structure causes fluid to be transported within a plane. Suitable capillary structures can be designed with advantageously low expenditure, in particular on a level upper face of the base body, for example by means of etching.

The base body of a lancet according to the invention can be designed integral with the lancing element, for example by cutting the contour of the base body, along with the lancing element originating therefrom, out of sheet metal, for example by means of laser cutting, stamping or etching. It is also possible, however, for the base body and the lancing element to be separate components, which are joined when producing the lancet.

According to a further advantageous refinement of the invention, the test region is disposed laterally offset with respect to the longitudinal direction of the lancing element by at least the width of the lancing element. The offset should be measured from the center of the lancing element to the center of the test region. In a region that adjoins the tip and is introduced into the skin of a patient during puncture, the lancing element preferably has a constant width, however it may also increasingly widen up to the base body. The decisive factor is the width of the lancing element at the end of the region introduced into the skin of patient as intended during a puncture.

According to a further advantageous refinement of the invention, the lancing element is disposed eccentrically on the base body, as viewed from above, which is to say the distance from the left edge of the base body differs from the distance from the right edge. In this way, a particularly compact lancet having a test region that is disposed laterally offset from the lancing element can be created. With a section carrying the test region, the base body can extend laterally from the lancing element by a greater distance than on the opposing side of the lancing element, for example by half more, twice as far, or even further.

According to a further advantageous refinement of the invention, the test region is designed as a glued-on test field containing detection reagents. Corresponding test fields containing detection reagents for photometrically or electrochemically determining an analyte concentration are available with commercially available test strips, for example to determine the glucose concentration, and therefore do not require any further explanation. Instead of a glued-on test field, the test region can also be designed as a cuvette, for example, in which a body fluid sample can be optically analyzed, notably it can be analyzed reagent-free.

BRIEF DESCRIPTION OF THE DRAWINGS

Further details and advantages of the invention will be described based on exemplary embodiments with reference to the attached drawings. Identical and corresponding parts are denoted with agreeing reference numerals. In the figures.

DETAILED DESCRIPTION

Figure 1:
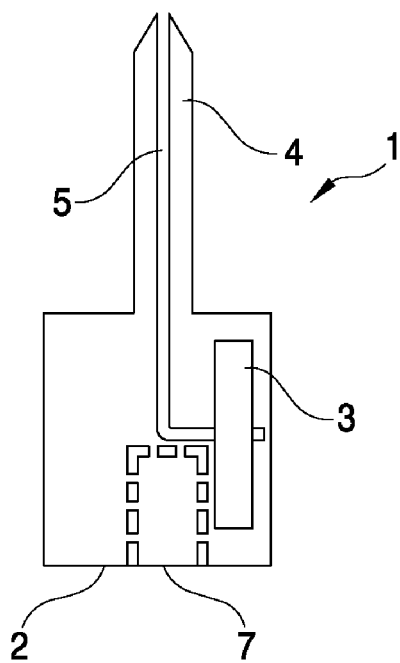
FIG. 1 is a schematic illustration of an embodiment of a lancet according to the invention in a top view of an upper face of the base body.

The lancet 1 shown in FIG. 1 comprises a base body 2 having a test region 3 for analyzing a body fluid sample, a lancing element 4 originating from the base body 2 for puncturing the skin of a patient, and a capillary structure 5 for transporting a body fluid sample from the lancing element 4 to the test region 3. The lancing element 4 extends in a longitudinal direction, which agrees with the piercing direction in which the lancet 1 performs a rectilinear piercing movement during use.

As viewed in the piercing direction, the lancing element 4 is disposed laterally offset from the test region 3. The capillary structure 5 thus comprises a section that causes fluid to be transported transversely to the piercing direction. In the embodiment shown, the section of the capillary structure 5 that runs transversely to the longitudinal direction of the lancing element 4 is disposed perpendicularly to the longitudinal direction of the lancing element 4. In principle, however, the section of the capillary structure 5 that runs transversely to the longitudinal direction of the lancing element 4 can also run obliquely to the longitudinal direction of the lancing element 4 or in a curved shaped.

Like the test region 3, the section of the capillary structure 5 that runs transversely to the piercing direction is disposed on the base body 2. The capillary structure 5 is preferably designed as a capillary channel, for example in the shape of a groove or a continuous slot. The capillary structure 5 extends from a front region of the lancing element, which is introduced into the body of a patient during a puncture, to the base body 2 and from there to the laterally offset test region. As is shown in FIG. 1, the capillary structure 5 is preferably open toward the tip. However, it is also possible for the capillary structure 5 to only start right behind the tip in a region which is introduced into the body of a patient during a puncture.

In the lancing element 4 and in an adjoining region of the base body 2, the capillary structure 5 runs in a rectilinear manner in the piercing direction. The capillary channel 5 thus has a bend or a curve. The straight starting section of the capillary structure 5 that runs in the lancing element 4 defines a geometrical straight line, which passes the test region 3 at a distance. The test region 3 is disposed laterally offset from the lancing element 4 with respect to the longitudinal direction of the lancing element 4. In this way, as viewed in the piercing direction, space remains laterally next to the test region 3 for a coupling region 7 for coupling the lancet 1 to a lancing drive of a hand-held device. The coupling region 7 indicated in FIG. 1 by an interrupted line can be designed as a coupling surface, which does not differ from the remaining surface of the base body 2, or it can be provided with a coupling structure, for example it may comprise flutes or other depressions.

Advantageously, the coupling region 7 is disposed such that a geometrical straight line, which is defined by the starting section of the capillary structure 5, intersects the coupling region 7. The test region 3 is disposed laterally adjacent to the coupling region 7 with respect to the longitudinal direction of the lancing element 4.

The base body 2 of the lancet 1 preferably has a plate-shaped design. In the embodiment shown, the capillary structure 5 in the upper face of the base body 2 is therefore arranged in a plane in the embodiment shown and causes liquid to be transported in a plane, which is to say on the substantially flat upper face of the base body 2.

For example, the contour of the base body 2, along with the lancing element 4 originating therefrom, can be cut out of sheet steel to produce the lancet 1. However, it is also possible to produce the base body 2 and the lancing element 4 separately and to join them when producing the lancet 1.

Figure 2:
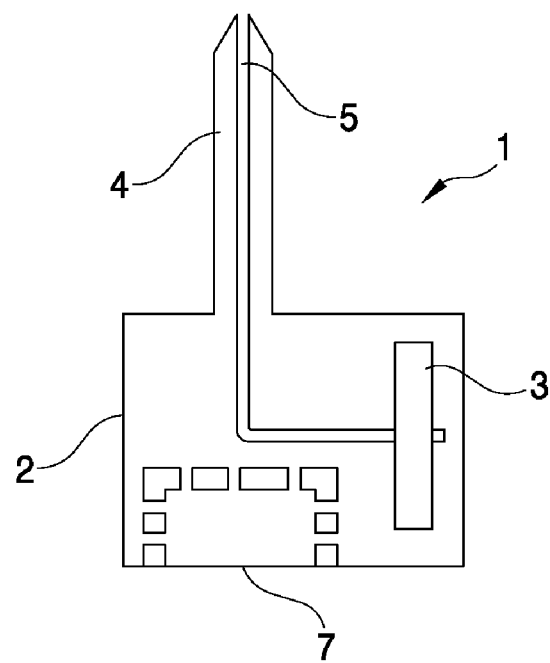
FIG. 2 is a schematic illustration of another embodiment of a lancet according to the invention.
Figure 3:
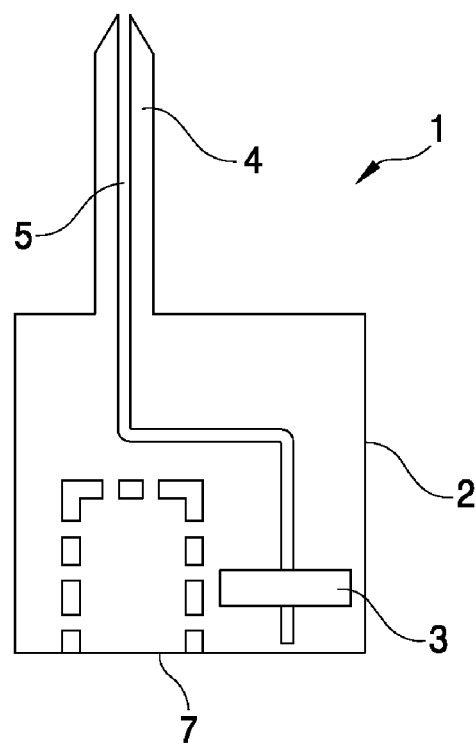
FIG. 3 is a schematic illustration of another embodiment of a lancet according to the invention.

FIGS. 2 and 3 show other embodiments of a flat lancet 1. Like in the embodiment shown in FIG. 1, the lancing element 4 is disposed laterally next to the test region 3, as viewed in the piercing direction. In the embodiments of FIGS. 2 and 3, however, the lancing element 4 does not originate centrally from one side of the base body 2. Instead, the lancing element 4 is disposed laterally offset on the base body 2.

In the embodiments shown in FIGS. 2 and 3, with the section carrying the test region 3, the base body 2 extends laterally from the lancing element 4 at least twice as far as on the opposing side of the lancing element 4. In the embodiments of FIGS. 2 and 3, on the side of the lancing element 4 on which the test region 3 is disposed, the base body 2 extends more than twice as far as on the other side of the lancing element 4. It is preferable for the base body 2 to extend laterally from the lancing element 4 on both sides, as is shown in FIGS. 2 and 3. However, in principle it is also possible for the base body 2 to extend transversely to the piercing direction only on one side of the lancing element 4 and to end flush with the lancing element 4 on the other side.

Each lancet 1 preferably has only a single test region 3. In the embodiments shown, this region is configured as a test field that contains detection reagents and is glued onto an upper face of the base body. In the embodiment shown, the capillary structure 5 leads from the lancing element 4 to the test region 3 and extends beyond the test region 3, so that the test region 3 can take up a body fluid sample particularly efficiently. The test region 3 is preferably designed in a strip shape, as shown in the figures.

Figure 4:
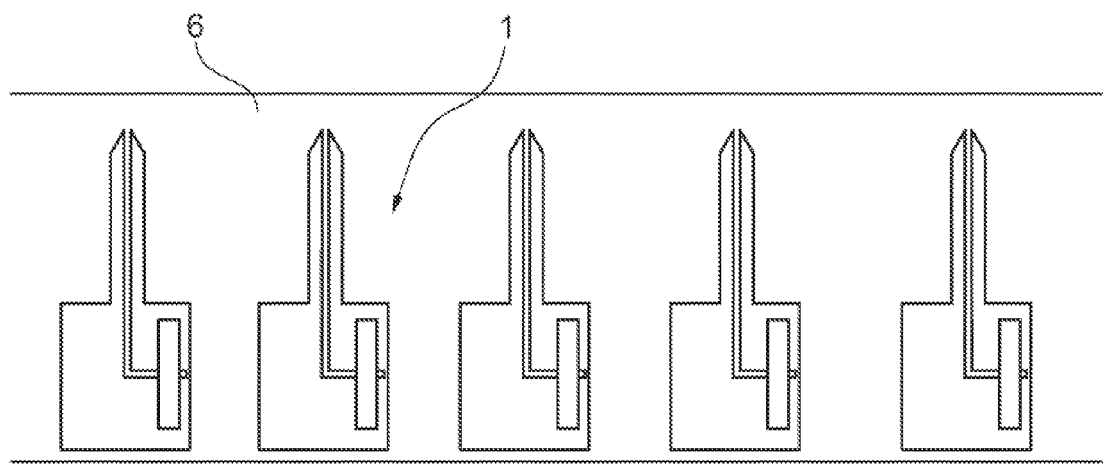
FIG. 4 is a schematic illustration of another carrier tape comprising a plurality of lancets according to FIG. 1.

FIG. 4 shows a schematic illustration of a lancet carrier tape 6 carrying a plurality of flat lancets 1, which can be designed, for example, as shown in FIG. 1. In the embodiment shown, the lancets 1 are oriented transversely to the longitudinal direction of the carrier tape 6, or more precisely, perpendicularly to the longitudinal direction. Such a lancet carrier tape 6 can be distributed, for example, in a tape cassette, which is inserted in a suitable receiving compartment of the device.

Figure 5:
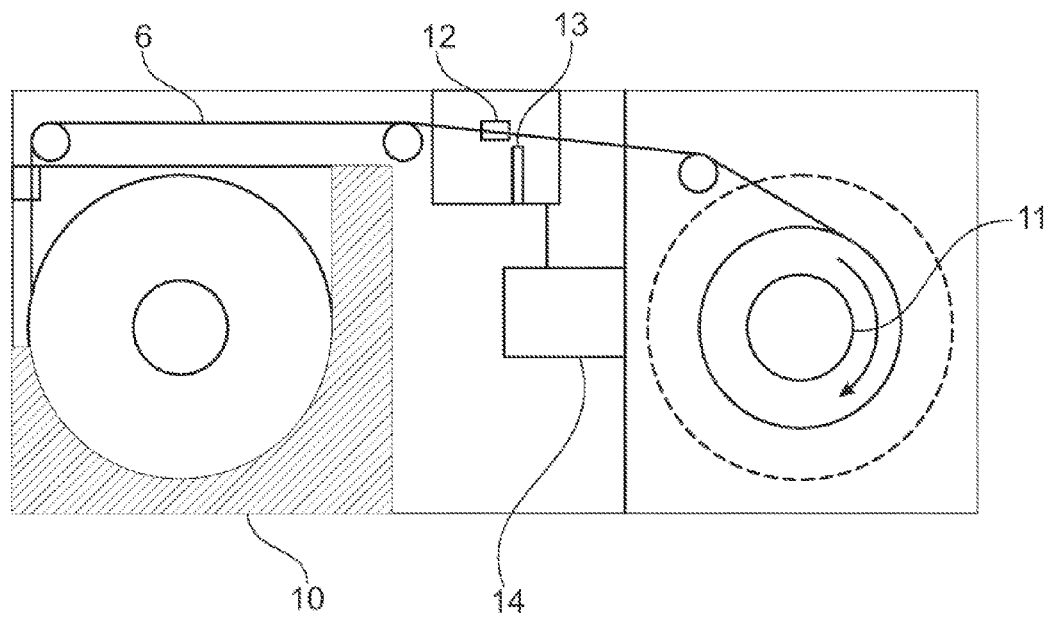
FIG. 5 is a schematic illustration of an embodiment of a lancing system.

FIG. 5 shows a schematic illustration of a lancing system, which comprises a hand-held device 10 and lancets 1, as those described above by way of example. A lancet carrier tape 6 comprising lancets 1 is disposed in the lancing device 10. The hand-held device 10 has a winding system 11 so as to incrementally wind the carrier tape 6 and thereby consecutively move the lancets 1 carried by the carrier tape 6 into a usage position, in which they can be caused to perform a rectilinear piercing movement by a lancing drive 12. The lancing drive 12 has a lancet holder so as to clamp a lancet 1, together with the carrier tape section carrying the same. In the embodiment shown, the piercing direction is perpendicular to the drawing plane. During a puncture, the lancet carrier tape 6 is bent, whereby the tip of the lancing element 4 is lifted off the carrier tape 6, as is known from WO 2008/083844 A1.

The lancing device 10 further comprises a measuring unit 13 for analyzing a body fluid sample in the test region 3. Because the test region 3 of the lancets 1 is disposed laterally offset behind the lancing element 4, as viewed in the piercing direction, the lancet holder leaves the test region 3 of a held lancet 1 exposed. In this way, the test region 3 and a sample received by the same can be analyzed by a measuring unit 13, for example by way of a photometric measurement, while the lancet 1 is being held by the lancet holder.

The measuring unit 13 and the lancing drive 12 can be connected to a control and evaluation unit 14, which evaluates measurements and displays measurement results on a display unit, for example a liquid crystal display.

REFERENCE NUMERALS

1 Lancet
2 Base body
3 Test region
4 Lancing element
5 Capillary structure
6 Lancet carrier tape
7 Coupling region
10 Hand-held device
11 Winding system
12 Lancing drive
13 Measuring unit
14 Control and evaluation unit

The invention claimed is:

1. A lancet, comprising
a base body, which has a test region on an upper face for analyzing a body fluid sample,
a lancing element extending from the base body for puncturing the skin of a patient, and
a capillary structure for transporting a body fluid sample from the lancing element to the test region, wherein at least a section of the capillary structure is a capillary channel, and wherein
in a top view of the upper face, the test region is disposed laterally offset in relation to the longitudinal direction of the lancing element, and the capillary structure has a section that is configured to transport fluid sideways, and wherein
the base body comprises a coupling region for coupling the lancet to a lancing drive of a hand-held device,
a rectilinear starting section of the capillary structure is arranged in the lancing element, and
the coupling region is disposed so that a geometrical straight line, which is defined by the starting section of the capillary structure, intersects the coupling region, wherein
the capillary channel has a bend with rounded corners or a curve and a cross-sectional surface, in the region of the bend or curve, that is no larger than in an adjoining section, and wherein
the coupling region is disposed in a straight line behind the lancing element and laterally beside the test region.

2. The lancet according to claim 1, wherein the test region is disposed laterally offset by at least the width of the lancing element with respect to the longitudinal direction of the lancing element.

3. A lancet according to claim 1, wherein the base body is plate-shaped.

4. A lancet according to claim 1 wherein the capillary structure is configured to cause fluid to be transported in a plane.

5. A lancet according to claim 1, wherein the base body is integral with the lancing element.

6. The lancet according to claim 1, wherein
the test region is disposed such that the geometrical straight line, which is defined by the starting section of the capillary structure, passes the test region at a distance.

7. A lancet according to claim 1, wherein the lancing element is disposed eccentrically on the base body.

8. A lancet according to claim 1, wherein the lancet comprises only a single test region.

9. A lancet carrier tape, comprising a plurality of lancets according to claim 1 disposed on the carrier tape.

10. A lancing system, comprising
lancets according to claim 1, and
a lancing device, which comprises a lancing drive so as to cause the lancets to perform a rectilinear piercing movement, and a measuring unit for analyzing a body fluid sample in the test region.

\* \* \* \* \*